United States Patent [19]
Uomori et al.

[11] Patent Number: 5,382,989
[45] Date of Patent: Jan. 17, 1995

[54] APPARATUS FOR EXAMINING GAZE SHIFT IN DEPTH DIRECTION

[75] Inventors: Kenya Uomori; Mitsuho Yamada; Hitoshi Hongo; Hiroshi Yoshimatsu; Keiichi Ueno, all of Kyoto; Shinji Murakami, Hokkaido; Mitsuru Fujii, Hokkaido; Norihito Nakano, Hokkaido; Jiro Miyazawa, Hokkaido; Ryo Fukatsu, Hokkaido; Naohiko Takahata, Hokkaido, all of Japan

[73] Assignee: ATR Auditory and Visual Perception Research Laboratories, Kyoto, Japan

[21] Appl. No.: 31,973

[22] Filed: Mar. 16, 1993

[30] Foreign Application Priority Data

Sep. 17, 1992 [JP] Japan .................. 4-247780

[51] Int. Cl.⁶ .................. A61B 3/10; A61B 3/14
[52] U.S. Cl. .................. 351/209; 351/210; 351/211; 351/221
[58] Field of Search .................. 351/205, 209, 210, 211, 351/221, 201

[56] References Cited

U.S. PATENT DOCUMENTS

| | | | |
|---|---|---|---|
| 2,168,308 | 8/1939 | Ames, Jr. | 351/201 |
| 3,609,016 | 9/1971 | Jampolsky | 351/209 |
| 4,528,989 | 7/1985 | Weinblatt | 351/210 |
| 4,838,681 | 6/1989 | Pavlidis | 351/211 |
| 4,889,422 | 12/1989 | Pavlidis | 351/210 |
| 4,958,925 | 9/1990 | Ober et al. | 351/210 |
| 5,260,734 | 11/1993 | Shindo | 351/210 |

FOREIGN PATENT DOCUMENTS

| | | | |
|---|---|---|---|
| 250657 | 10/1987 | Germany | 351/201 |
| 4-272743 | 9/1992 | Japan | 351/209 |
| 2103045 | 2/1983 | United Kingdom | 351/209 |
| 625687 | 8/1978 | U.S.S.R. | 351/209 |

OTHER PUBLICATIONS

M. Yamada et al. "Development of an Eye-Movement Analyser Possessing Functions for Wireless Transmission and Autocalibration" Medical and Biological Engineering and Computing, Jul. 1990, pp. 317-324.

Primary Examiner—Richard A. Bertsch
Assistant Examiner—Howard R. Richman
Attorney, Agent, or Firm—Lowe, Price, LeBlanc & Becker

[57] ABSTRACT

In an apparatus for examining gaze shift in depth direction, light emitting diodes B and E, or D and C are lit at a plurality of positions with different distance in depth direction from the subject, and eye movement of the subject at that time is detected by an eye movement detecting portion. The signal of detection is processed in a signal processing circuit and is applied to a calculating portion. The calculating portion determines whether or not there is a disorder in gaze shift in depth direction of the subject by using any or all of latency in eye movement, time constant, amplitude, change in convergence angle, number of occurrence of saccade, and asymmetry of left and right eye movements, in response to the detected output of the eye movement.

6 Claims, 12 Drawing Sheets

LED ON
(ALARM SOUND)

LED ON
(ALARM SOUND)

X Y Z COORDINATE SYSTEM

POLE COORDINATE SYSTEM

APPARATUS FOR EXAMINING GAZE SHIFT IN DEPTH DIRECTION

BACKGROUND OF THE INVENTION

1. Field of the Invention

The present invention relates to an apparatus for examining gaze shift in the depth direction. More specifically, the present invention relates to an apparatus for examining gaze shift in the depth direction thereby enabling the determination of diseases related to brain functions, such as dementia, by detecting gaze shift of a subject.

2. Description of the Background Art

The number of patients suffering from Alzheimer's disease is estimated to be four million in the United States and about a million in Japan. Compared with senile dementia, such as cerebrovascular disease popular among Japanese, the cause of Alzheimer's disease is not known, and much effort has made to find the cause to enable early diagnosis and early medical treatment. However, it is difficult to discriminate Alzheimer's disease from cerebrovascular disease when there are no typical symptoms. There has been a strong demand of accurate method of discrimination, since the development of the disease and its pharmaceutical treatment are different for these diseases.

Hachinski's ischemic score has been proposed as a method of discriminating these two diseases. According to this ischemic score, a point is given dependent on whether or not the patient has an anamnesis of apoplexy, cerebral infraction or the like, and if the points exceed a prescribed number, it is determined as the cerebrovascular disease, and otherwise it is determined to be Alzheimer's disease. However, discrimination is still difficult by this method if the patient has no such anamnesis.

It has been known that neuropsychological symptom which is considered to be an impairment of "tool function," such as visual cognitive dysfunction, appears from relatively early period of Alzheimer's disease. In view of this fact, Fujii et al. has reported the following analysis carried out by utilizing eye movement. More specifically, a problem of copying a cube on the right side while watching an original of the cube on the left side is presented. Even a patient who is in the initial stage I of Alzheimer's disease and does not show apparent constructional apraxia is reported to show characteristic symptom similar to a so called Balint syndrome; that is, the patient cannot stare at one point, or more specifically, abnormal distribution of gazing point appears, saccade deviated from both the presented cube and the depicted drawing by the patient is generated, or the point of gazing is fixed at the same point for a long period of time. In Alzheimer's disease, it is supposed from MRI (nuclear magnetic periorbital inspection) that there is caused dysfunction of parietal lobe which is related to spatial vision. Accordingly, constructional dysfunction derived from degradation in function of the rear association areas with the parietal lobe being the center, degradation of function of positional recognition of a target point or recognition of depth derived from dysfunction of external spatial vision, such as dysfunction of eye movement, dysfunction of coordinate transformation system between the coordinate of eye movement system and the coordinate of the center of one's body axis, or visual-motor dysfunction, is supposed to be a possible cause of the aforementioned symptoms.

SUMMARY OF THE INVENTION

Therefore, an object of the present invention is to provide an apparatus for examining gaze shift in the depth direction allowing determination of dysfunction in depth perception or in eye movement control mechanism by detecting gaze shift in the depth direction of the subject.

Briefly stated, in the present invention, a target for depth perception is presented to a subject, movement of left and right eye balls of the subject gazing at the target are detected, and a disorder in gaze shift in the depth direction of the subject is detected on the basis of the detected output.

Therefore, according to the present invention, disorder of the eye movement control mechanism, of depth perception and position in the brain of the subject can be readily detected, which allows discrimination of Alzheimer's disease from cerebral vascular disease.

In a preferred embodiment, head movement of the subject is detected and characteristics of gaze shift is determined on the basis of head movement and eye movement.

According to a more preferred embodiment, disorder in gaze shift in depth direction is determined by using any of or all of latency in gaze shift, time constant, amplitude, change in convergence angle, number of saccades and asymmetry of left and right eye movements as characteristics of gaze shift.

The foregoing and other objects, features, aspects and advantages of the present invention will become more apparent from the following detailed description of the present invention when taken in conjunction with the accompanying drawings.

DESCRIPTION OF PREFERRED EMBODIMENTS

Figure 1:
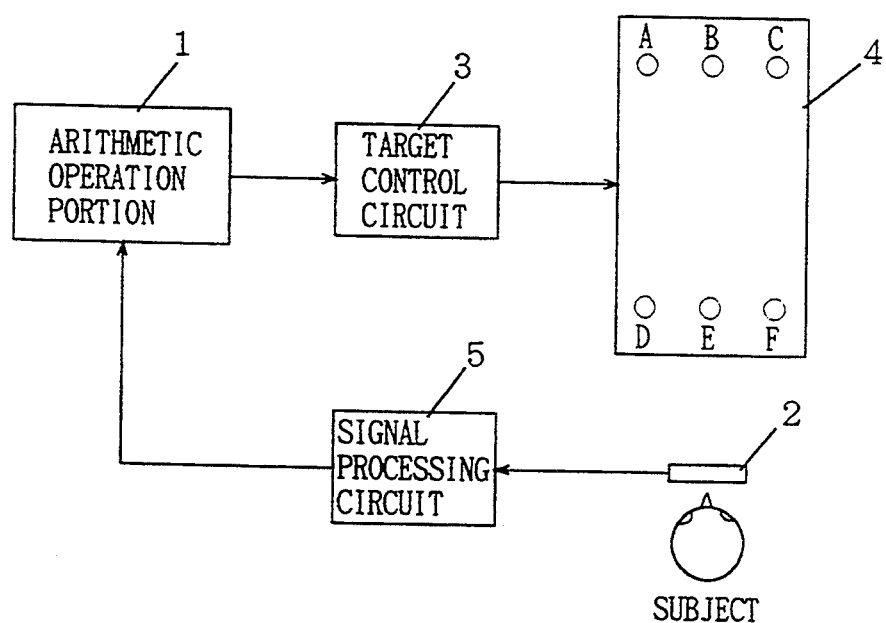
FIG. 1 is a schematic block diagram of one embodiment of the present invention.

FIG. 1 is a schematic block diagram of one embodiment of the present invention.

Referring to FIG. 1, an eye movement detecting portion 2 detects eye movement of a subject, and the output of detection is applied to a signal processing circuit 5 to be processed and applied to an arithmetic operation portion 1. A personal computer or a work station is used as the arithmetic operation portion 1. A target control circuit 3 lights targets on a plate for calibration 4 in accordance with an instruction from the arithmetic operation portion 1. In this example, three light emitting diodes A, B and C are provided distant from the subject and three light emitting diodes D, E and F are provided near the subject, on the plate 4. The target is not limited to the diodes, and any means which can be recognized by the subject may be used. In accordance with the instruction from the arithmetic operation portion, the light emitting diodes are lit in the order of A→F, B→E and C→D, for example, and the eye movement of the subject at that time is detected by the eye movement detecting portion.

Figure 2:
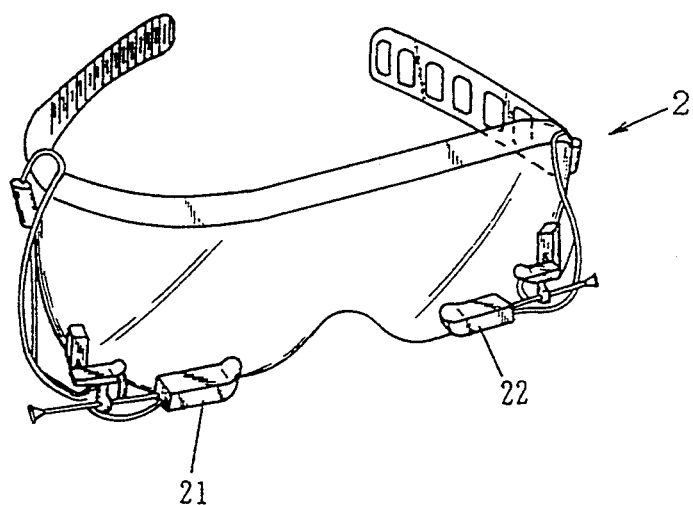
FIG. 2 shows a specific example of the eye movement detecting portion.
Figure 3:
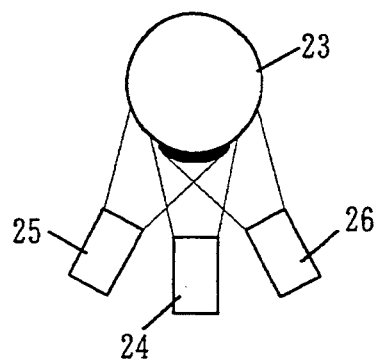
FIGS. 3(a), 3(b) an 3(c) show the operation of the eye movement detecting portion.
Figure 3:
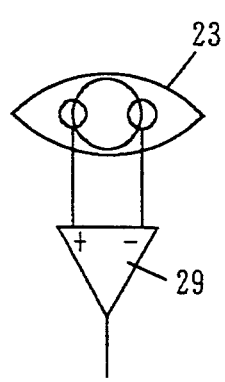
Figure 3:
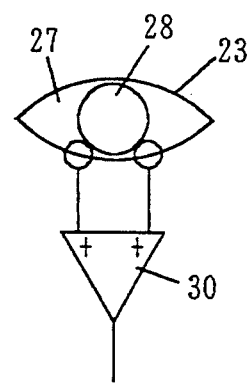

FIG. 2 shows a specific example of the eye movement detecting portion shown in FIG. 1, and FIG. 3 shows the operation of the eye movement detecting portion.

Referring to FIG. 2, the eye movement detecting portion 2 is attached to goggles, and the subject wears the goggles. The eye movement detecting portion 2 utilizes limbus reflection method and provided with detecting portions 21 and 22 for detecting movement of left and right eyes. The detecting portions 21 and 22 each include a light emitting diode 24 provided centered with respect to the eye ball 23 and photodiodes 25 and 26 provided on both sides of the diode 24. A light emitting diode radiating infrared rays having relatively wide directivity of about ±21° is used as the light emitting diode 24, while ones having acute directivity of about ±10° are used as the photodiodes 25 and 26. The light beam emitted from the light emitting diode 24 to the eye ball 23 is reflected from the iris of the eye 28 and from the white of the eye 27 with different reflectivity, and the difference in reflectivity is amplified by an operational amplifier 29. If the difference is calculated, a horizontal output (left and right) is obtained as shown in FIG. 3(b), and if the sum is calculated by an operation amplifier 30, a vertical (up and down) output is obtained as shown in FIG. 3(c).

The eye movement detecting portion 2 may utilize a contact lens (the search coil method) or a TV camera (the cornea reflection method), other than the aforementioned limbus reflection method.

Figure 4:
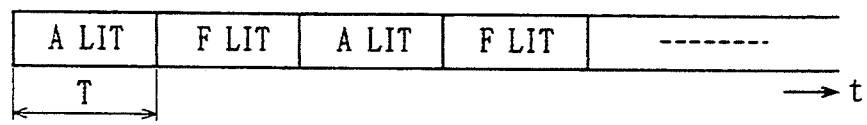
FIGS. 4(a), 4(b) and 4(c) are diagrams for describing the sequence of lighting light emitting diodes on a board for calibration.
Figure 4:
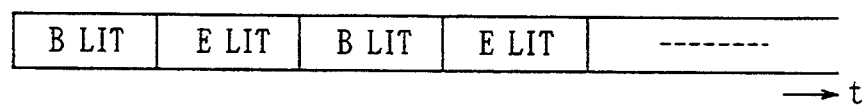
Figure 4:
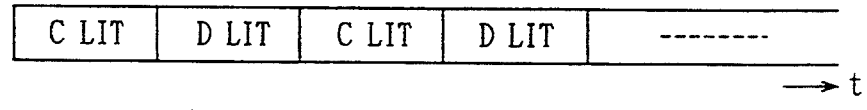
Figure 5:
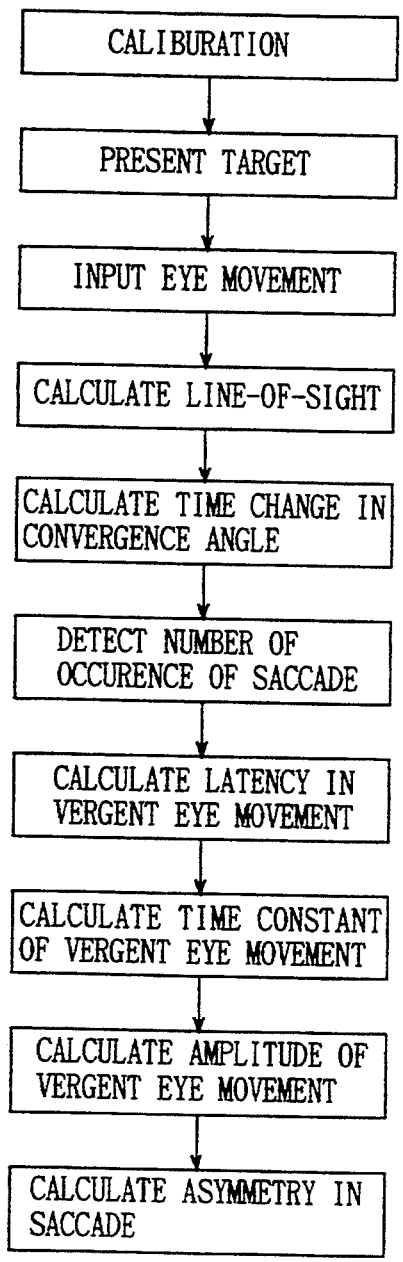
FIG. 5 is a flow chart showing specific operation of one embodiment of the present invention.

FIG. 4 shows a lighting sequence of the light emitting diodes on the board for calculation, and FIG. 5 is a flow chart showing a specific operation of one embodiment of the present invention.

A specific operation of one embodiment of the present invention will be described with reference to FIGS. 1 to 5. First, the subject wears the goggles provided with the eye movement detecting portion 2 shown in FIG. 2 on his head. In order to fix the head of the subject, a head-chin rest or a bite board is used. The calibration is effected. This is because that detection output of the eye movement detecting portion differs subject by subject. Details of the calibration is disclosed in *Medical and Biological Engineering and Computing* July 1990. More specifically, in place of the board for calibration 4, a calibration board provided with a plurality of light emitting diodes arranged in the periphery is prepared. The light emitting diodes are lit successively, the level of detection output from the eye movement detecting portion 2 at that time is determined, and the level is adjusted such that a prescribed output is obtained from a signal processing circuit 5.

Then, the arithmetic operation portion 1 gives an instruction to the target control circuit 3 to light light emitting diodes of the board 4, and thus presents a target. The presentation of the target is carried out such that a light emitting diode A arranged at a distant and a light emitting diode F arranged close to the subject are lit alternately. In this embodiment, there are three combinations of close and distant targets, that is, the diodes A and F, B and E, and C and D as shown in FIG. 4. However, the number and the combination of the targets may be increased or decreased. Further, when the target is lit, an alarm sound may be given so as to attract attention of the subject. In this manner, eye movement of the subject when the gaze is shifted in the depth direction is measured, and the result of measurement is stored in a memory device (hard disc, floppy disc or the like) included in the arithmetic operation portion 1. The measured eye movement is analyzed by the arithmetic operation portion 1.

Figure 6:
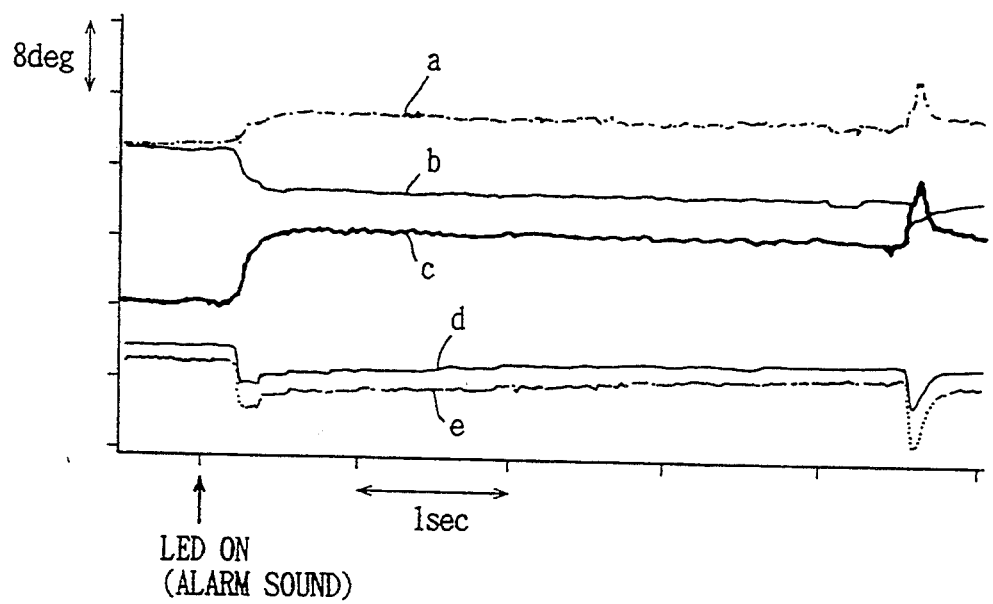
FIG. 6 shows an example of a display of eye movement of a healthy person when the target is moved from B to E.
Figure 7:
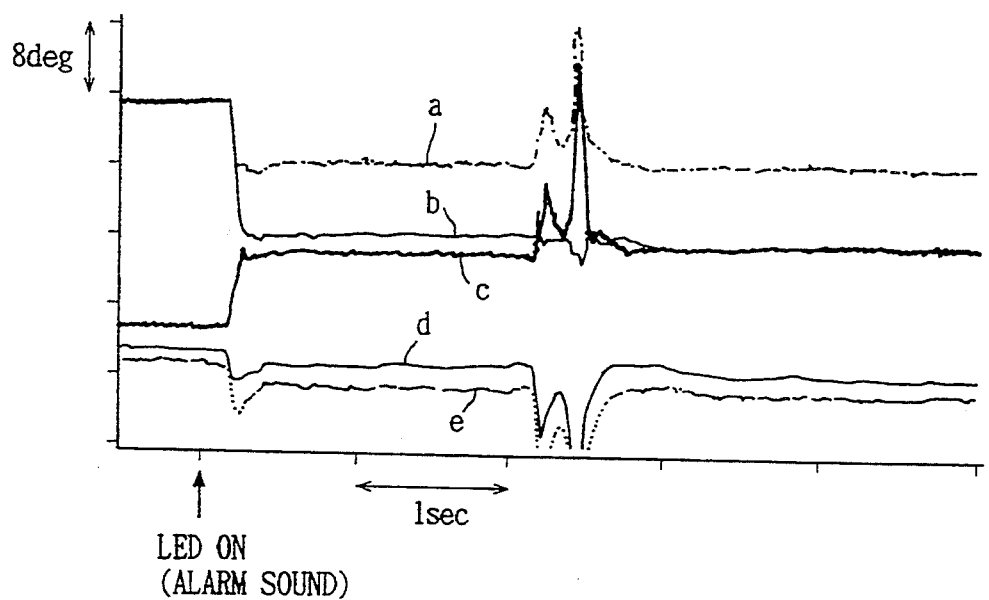
FIG. 7 shows an example of a display of a healthy person's eye movement when the target is moved from C to D.

FIGS. 6 to 17 shows example of measurement in accordance with one embodiment of the present invention. FIG. 6 is an example of display of eye movement of a healthy person when the target is changed from B to E, and FIG. 7 shows an example of display of the healthy person's eye movement when the target is changed to C to D. In FIGS. 6 and 7, the reference character a represents horizontal eye movement of the left eye, b represents horizontal eye movement of the right eye, c represents a change in convergence angle, d represents vertical eye movement of the right eye and e represents vertical eye movement of the left eye. In FIG. 6, the left and right eyes move in opposite directions, vergence eye movement which is a relatively slow movement is generated, the gazing is shifted from the distant point to the close point, and the convergence angle c is increased.

In the example shown in FIG. 7, the targets are arranged in asymmetry in left and right directions. Therefore, at first, very rapid eye movement called saccade is generated in asymmetry, then vergence movement, which is relatively slow eye movement occurs, increasing the angle of convergence.

Figure 8:
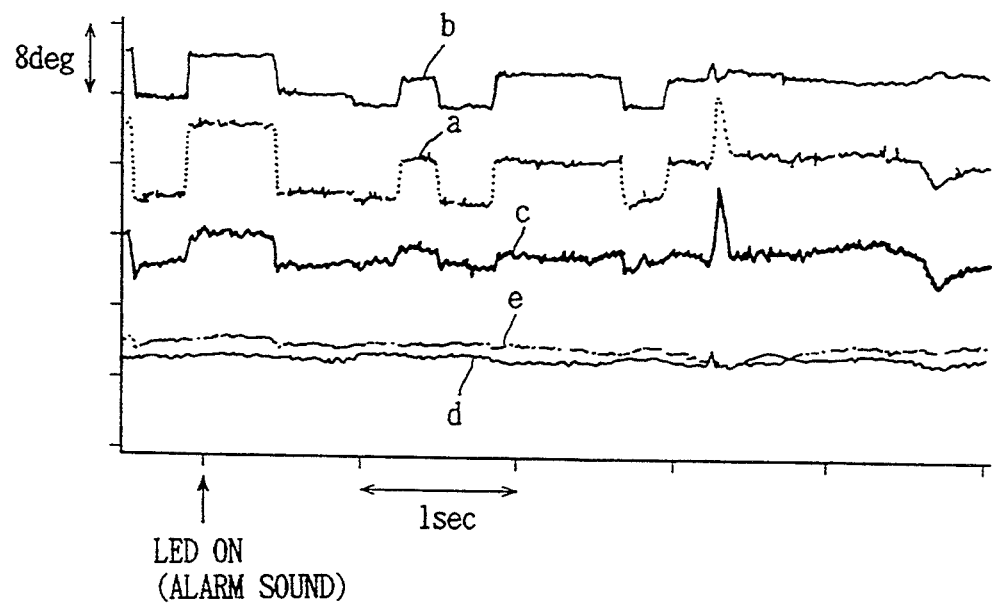
FIG. 8 shows an example of a display of eye movement of a patient in a moderate stage of Alzheimer's disease, age 52, when the target is moved from B to E.
Figure 9:
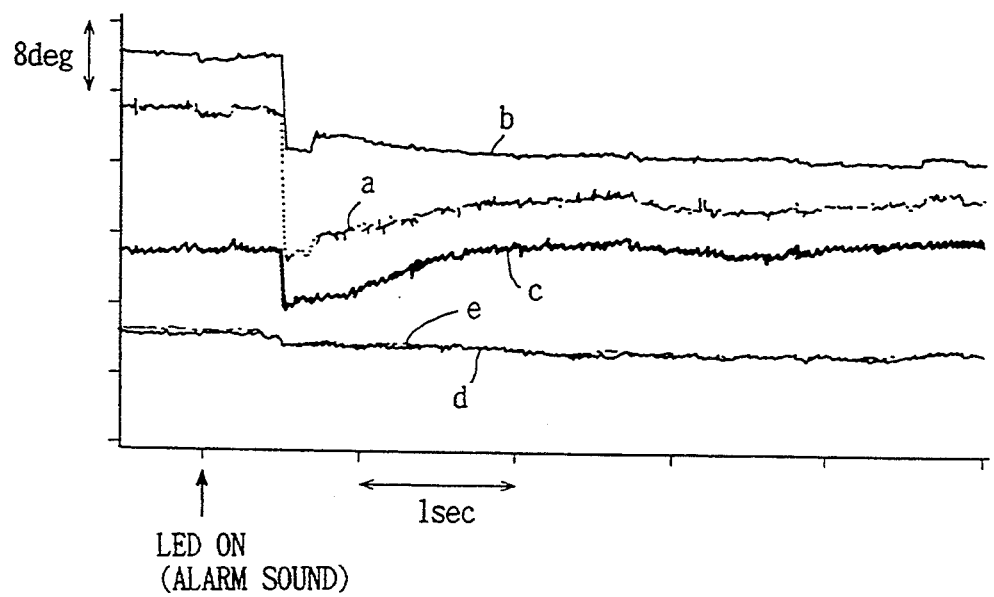
FIG. 9 shows an example of a display of the eye movement of a patient in a moderate stage of Alzheimer's disease, age 52, when the target is moved from C to D.

FIG. 8 shows an example of display of the eye movement of a patient in a moderate stage of Alzheimer's disease, age 52, when the target is moved from B to E. FIG. 9 shows an example of display of a patient in a moderate stage of Alzheimer's disease when the target is moved from C to D. As is apparent from the comparison between FIGS. 8 and 9 and FIGS. 6 and 7 above, the result of measurement of the patient suffering from Alzheimer's disease is considerably different from that of a healthy person. In the example of FIG. 8 in which symmetrical eye movement between left and right targets B an E is required, asymmetrical saccade which is rapid eye movement frequently occurs, and slow vergence eye movement is not so frequently observed. As for the change in the convergence angle c, the monotonous change as in a healthy person is not recognized and the amplitude thereof is small.

In the example of FIG. 9, asymmetrical saccade is generated at the initial stage of reaction, and then slow vergence eye movement occurs thereafter. As for the change in the convergence angle c, the angle c once decreases because of the asymmetrical saccade at first, and then vergence eye movement occurs as to compensate for the decrease. In this example, although the eye movement is from a distant point to a close point, the convergence angle c decreases once and the original angle is simply resumed.

Figure 10:
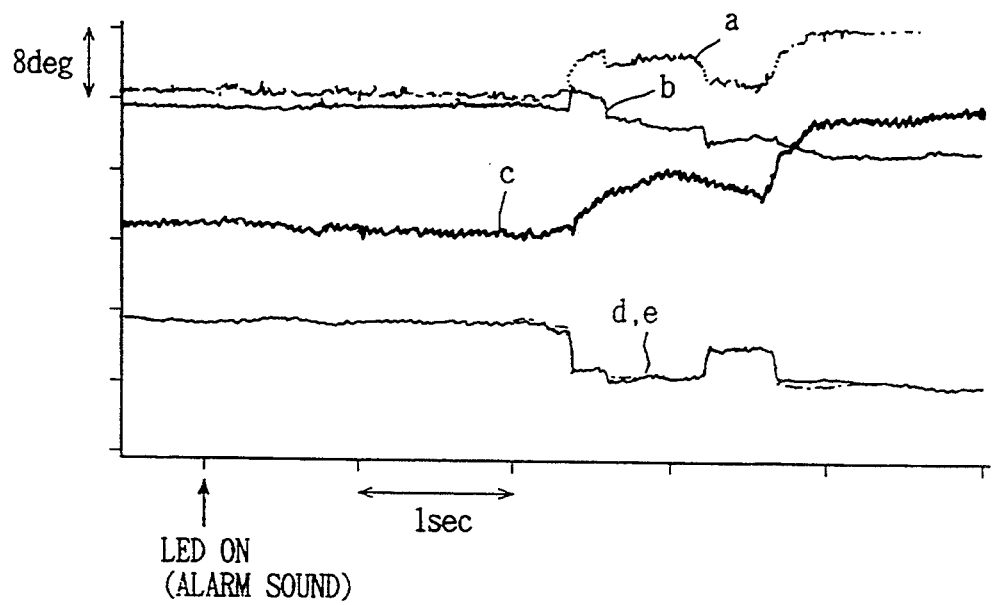
FIG. 10 shows an example of a display of the eye movement of a patient in a moderate stage of Alzheimer's disease, age 66, when the target is moved from B to E.
Figure 11:
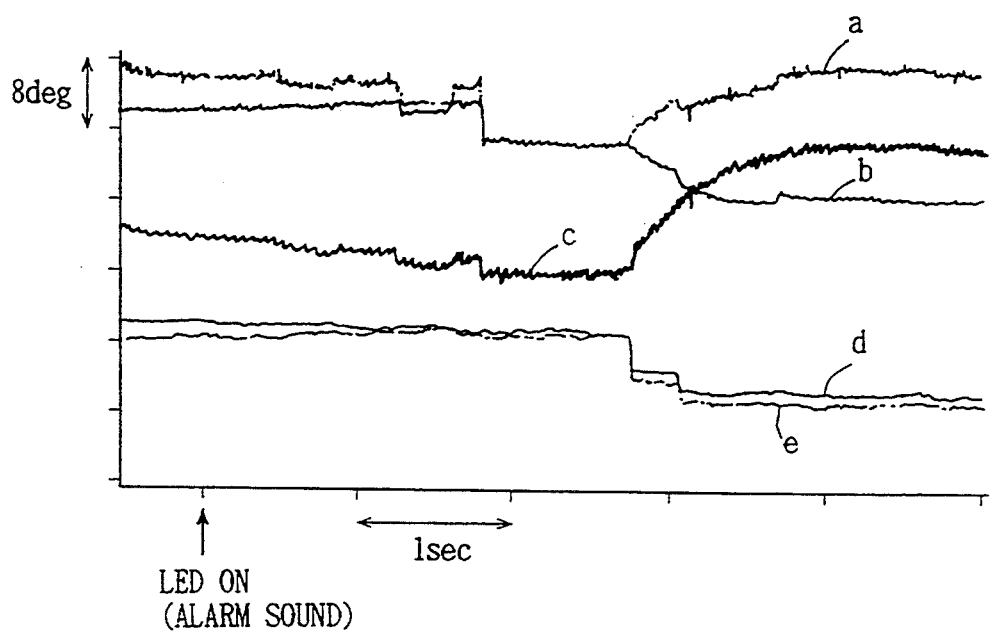
FIG. 11 shows an example of a display of the eye movement of a patient in a moderate stage of Alzheimer's disease, age 66, when the target is moved from C to D.

FIG. 10 shows an example of display of the eye movement of a patient in a moderate stage of Alzheimer's disease, age 66, when the target is moved from B to E. FIG. 11 is an example of display of the eye movement of the patient in a moderate stage of Alzheimer's disease when the target is moved from C to D. The reaction of this patient is little different from that of the patient of Alzheimer's disease discussed with reference to FIGS. 8 and 9. In the condition of FIG. 10 which requires symmetrical eye movement, saccade is not frequently observed in the initial stage of reaction but saccade is observed when vergence eye movement, which is the slow eye movement is generated. Start of the vergence eye movement is delayed very much as compared with the example of a healthy person shown in FIGS. 6 and 7. The change in the convergence angle is not monotonous but instable. Even in the target arrangement which is asymmetrically shown in FIG. 11, asymmetrical saccade is observed in the initial stage of reaction. However, though the condition is to move the eye from the distant point to the close point, the convergence angle reduces at first and after a considerable delay, a slow vergence eye movement occurs. As for the velocity of vergence eye movement, it is slower as compared with a healthy person discussed with reference to FIGS. 6 and 7.

From the results of measurement described above, frequent occurrence of saccade, increased latency in vergence eye movement, increase of time constant of the vergence eye movement, small amplitude and not monotonous change of convergence angle, asymmetrical saccade in the initial stage of reaction when symmetrical eye movement is required (for example, eye movement from the target B to E) may be regarded as particular characteristics of the eye movement of a patient suffering from Alzheimer's disease.

In view of the foregoing, in the present invention, the arithmetic operation portion 1 calculates the time change of the convergence angle, detects the number of occurrence of saccade, calculates latency of the vergence eye movement, calculates time constant of the vergence eye movement, calculates amplitude of the vergence eye movement, and calculates asymmetry of saccade, on the basis of the output from the eye movement detecting portion 2, in accordance with the manner shown in FIG. 5.

Figure 12:
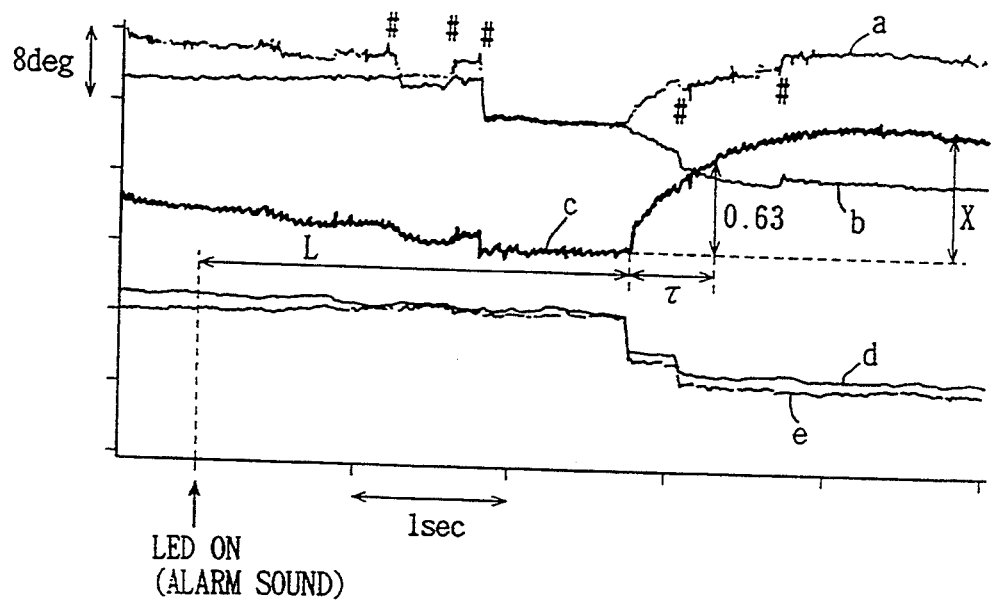
FIG. 12 shows an example of parameters of the eye movement.

FIG. 12 shows an example of parameters of the eye movement. Referring to FIG. 12, the number N of occurrence of saccade is obtained by calculating the number of saccade in a predetermined time period after lighting of the target. As for the method of detecting saccade, it can be easily detected by counting portion (denoted by #) where the eye moves rapidly from the graph of the eye movement shown in FIG. 12, by determining such portions with reference to the velocity of eye movement and so on.

The latency L of vergence eye movement means the time from lighting of target to the start of the movement of eye. In order to obtain latency, the convergence angle (the value of the angle in the direction of the left eye minus the value of the angle in the direction of the right eye) is calculated, and latency is obtained by subtracting the time of lighting the target from the time at which this value changes exceeding a certain threshold value (for example, about 0.5°). Alternatively, the change of the convergence angle (velocity or acceleration) may be calculated to find the time at which the eye movement starts on the basis of the calculated change of the convergence angle.

Assuming that the system for controlling eye movement is described in a first order lag system, then the time required for the eye movement to reach 63% of the final amount of change X ($=1-1/e$) at the rising portion of the whole eye movement of FIG. 12 corresponds to the time constant r of the vergence eye movement, and therefore, this time is measured.

As for the amplitude X of vergence eye movement, the change of the convergence angle is calculated and the amplitude when the change in the angle is not observed is measured. As shown in FIGS. 8 to 11, the change of the convergence angle is not monotonous in case of patients suffering from Alzheimer's disease, and therefore maximum value of amplitude may be used. As for the monotony of the change of the convergence angle, the time change of the convergence angle may be directly observed or velocity component or acceleration component may be calculated and whether such component changes frequently or not may determined.

Figure 13:
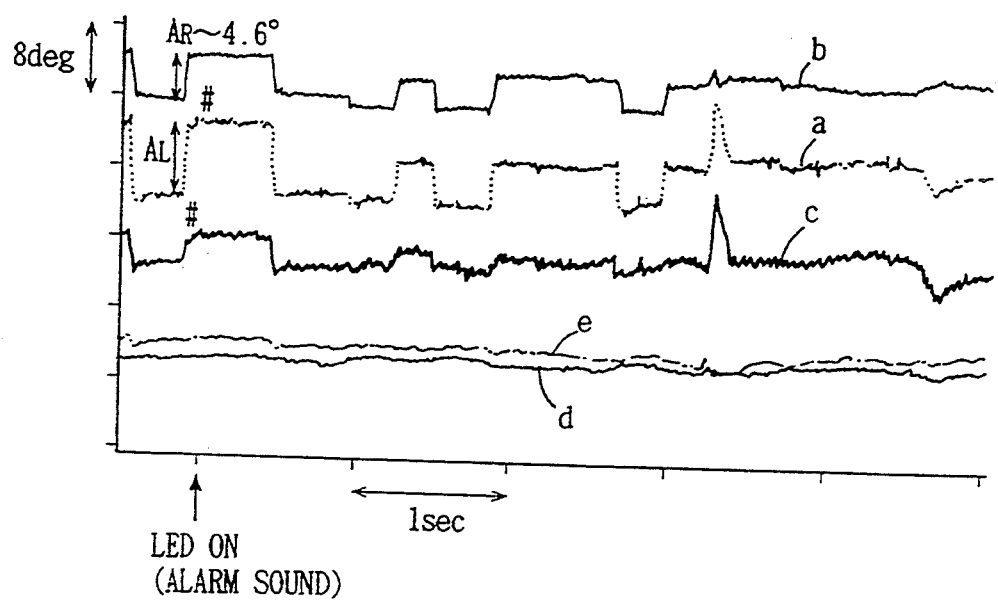
FIG. 13 shows an example of a measurement of asymmetry of left and right saccades of a patient suffering from Alzheimer's disease.

FIG. 13 shows an example of measurement of asymmetry in left and right saccade of a patient suffering from Alzheimer's disease. Asymmetry of saccade in the initial stage of reaction may be calculated by finding amplitudes AL and AR of the saccade by employing the aforementioned method of detecting saccade, and by calculating the asymmetry Asym of the left and right saccade in accordance with the following expression:

$$Asym = (AL - AR)/(AL + AR)$$

Generally, saccade in eye movement on a line in front of one's face is symmetrical in left and right directions and therefore Asym $\sim 0$. However, in case of a patient suffering from Alzheimer's disease, the value of Asym is not 0, as shown in FIG. 13.

Alternatively, a higher order lag system may be defined as a mechanism for controlling eye movement, parameters may be fitted approximately on a curve on the basis of the measured waveform, and latency of vergence eye movement, constant and amplitude may be calculated on the basis of the values of the parameters.

Figure 14:
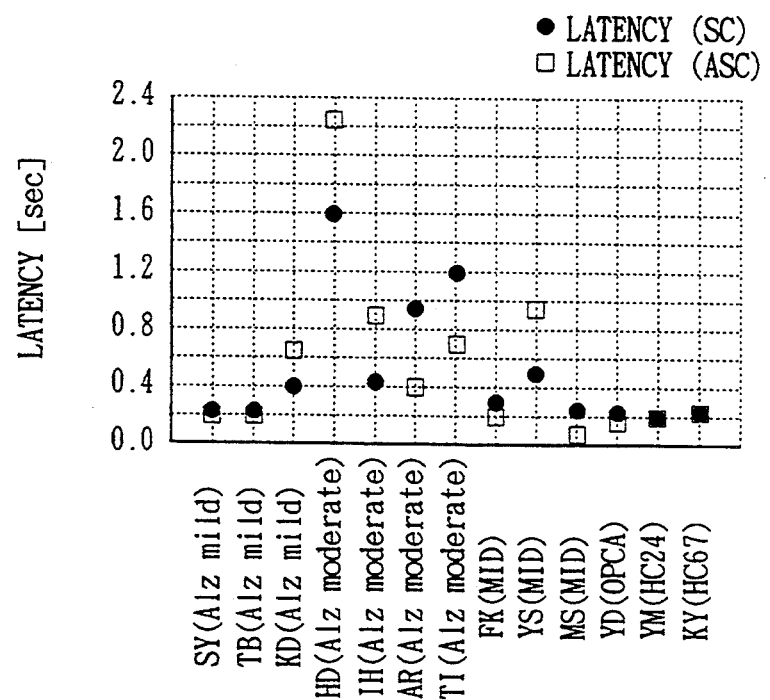
FIG. 14 shows latency of vergence eye movement measured.
Figure 15:
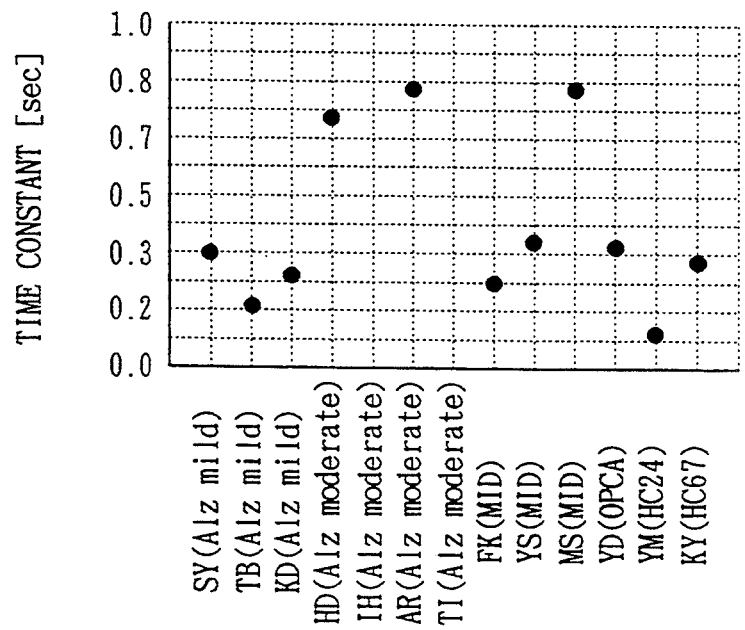
FIG. 15 shows time constant of the vergence eye movement.
Figure 16:
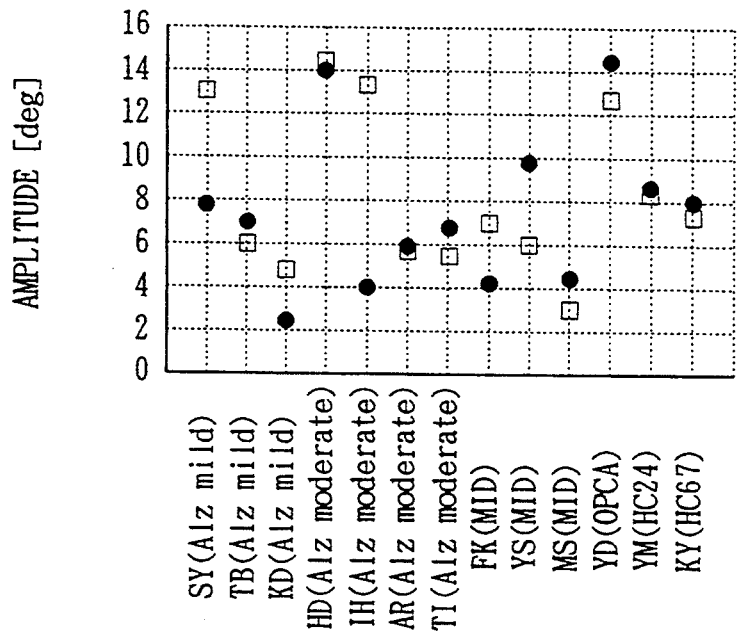
FIG. 16 shows amplitude of change in convergence angle.
Figure 17:
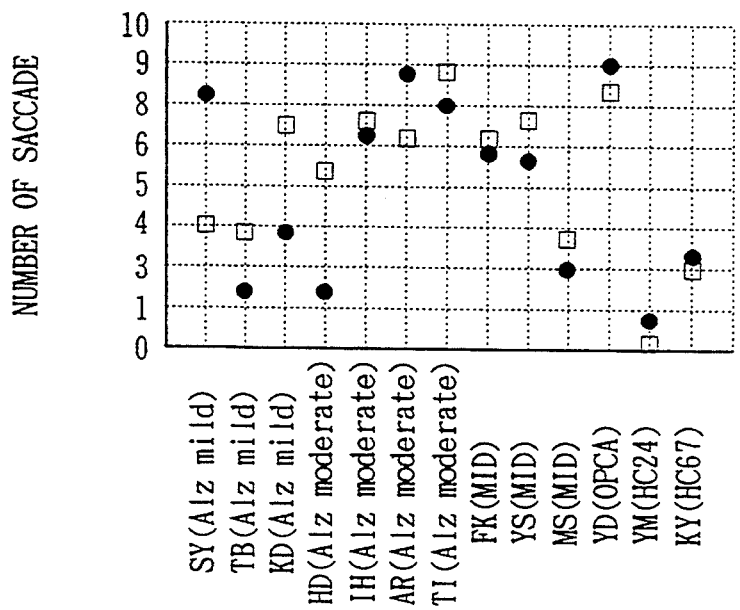
FIG. 17 shows number of saccades.

FIGS. 14 to 17 show examples of actually measured parameters in which FIG. 14 shows latency in vergence eye movement, FIG. 15 shows time constant, FIG. 16 shows amplitude and FIG. 17 shows the number of occurrence of saccade. In FIGS. 14 to 17, "Alz mild" represents a patient in a mild stage of Alzheimer's disease, "Alz moderate" represents a patient in a moderate stage of Alzheimer's disease, "MID" represents a patient suffering from multi-infarct dementia, "OPCA" denotes a patient suffering from olivopontocerebellar atrophy, and the remaining are healthy persons. As shown in FIG. 14, the latency of vergence eye movement of a patient suffering from Alzheimer's disease is long, and time constant is also long when the disease is advanced to a moderate stage. LATENCY (SC) represents the result of measuring gaze shift only in the depth direction, while LATENCY (ASC) represents the result of measuring gaze shift in the depth direction and gaze shift in the left and right directions. Generally, both SC and ASC of a patient suffering from Alzheimer's disease are larger than those of a healthy person. By measuring LATENCY SC and ASC, it becomes easier to specify the disorder only in the depth direction, or the fact that the patient can recognize changes in position in left and right directions but cannot easily recognize a change in position in the depth direction. The same applies to the change in time constant and in convergence angle as well. The amplitude of the change of the convergence angle of the patient suffering from Alzheimer's disease is smaller as shown in FIG. 16, and the number of occurrence of saccade tends to be increased as shown in FIG. 17. Since there are exceptions in each parameter, it may be difficult to discriminate Alzheimer's disease from other disease (MID.OPCA) or from the healthy person perfectly when only one parameter is used. However, discrimination of Alzheimer's disease can be done easily when all these parameters (latency, time constant, amplitude, number of saccades and asymmetry of the left and right eyes) are used for determination. More accurate discrimination can be realized if conventional Hachinski's ischemic score, computer tomography (CT) of the brain and so on are used in addition to the above described results of measurement.

Figure 18:
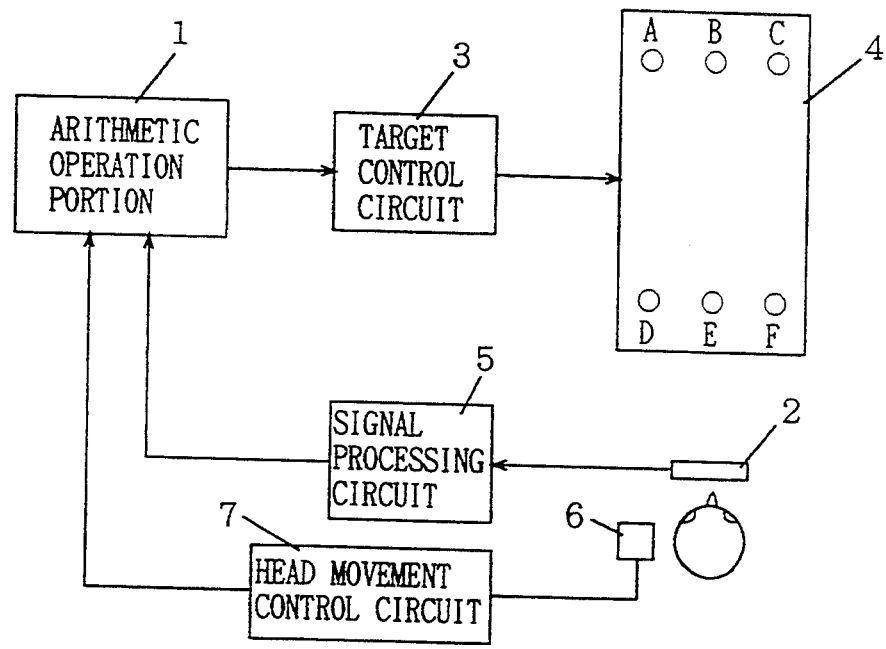
FIG. 18 is a block diagram showing another embodiment of the present invention.
Figure 19:
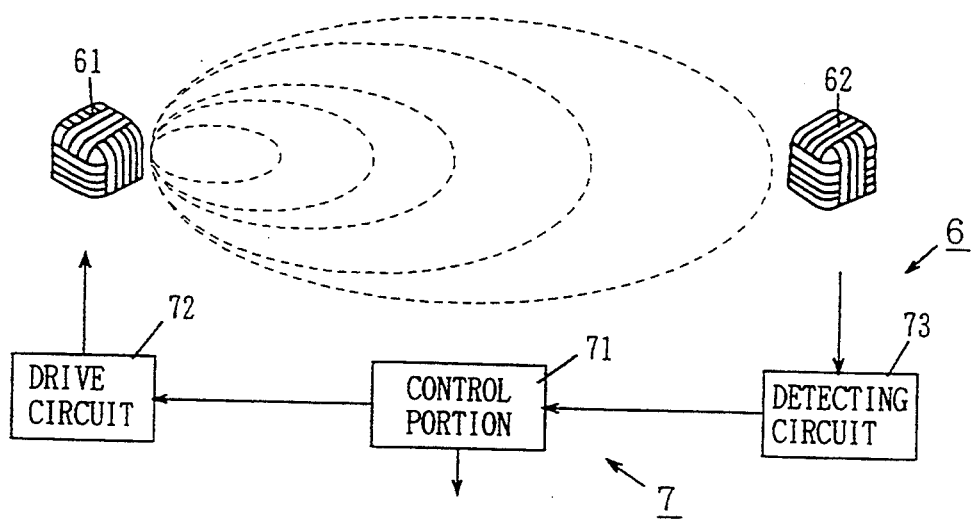
FIG. 19 shows a specific example of the head movement detecting portion shown in FIG. 18.

FIG. 18 is a block diagram showing another embodiment of the present invention and FIG. 19 shows a specific example of the head movement detecting portion shown in FIG. 18.

In the embodiment of FIG. 18, head movement of the subject is also detected. For this purpose, a head movement detecting portion 6 and a head movement control circuit 7 are provided. Except this point, the structure is the same as that shown in FIG. 1. The head movement detecting portion 6 includes an orthogonal coil serving as a source 61 and an orthogonal coil serving as a sensor 62 as shown in FIG. 19. The head movement control circuit 7 includes a control portion 71, a drive circuit 72 and a detecting circuit 73. The drive circuit 72 drives the orthogonal coil of the source 61 to generate a magnetic field in response to an instruction from the control portion 71. When the subject wearing the head movement detecting portion 6 moves, a voltage is induced in the sensor 62, the voltage is detected by the detecting circuit 73 and the detected output is calculated by the control portion 71, so that data corresponding to the movement of the head is output. The head movement detecting portion 6 is attached to the goggles shown in FIG. 2.

Figure 20:
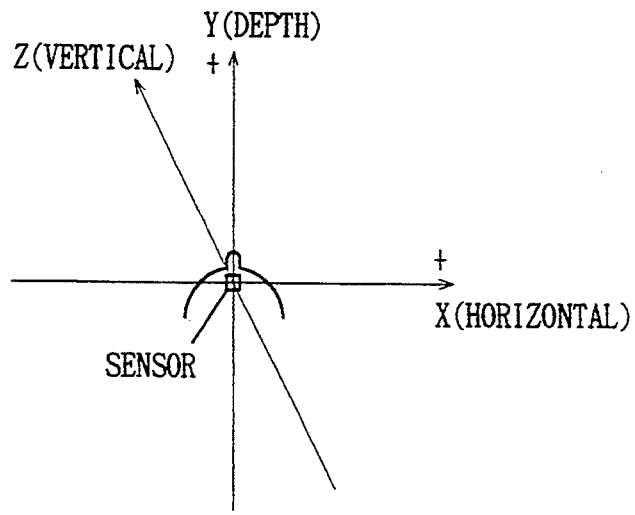
FIGS. 20(a) and 20(b) are illustrations of the head coordinate system.
Figure 20:
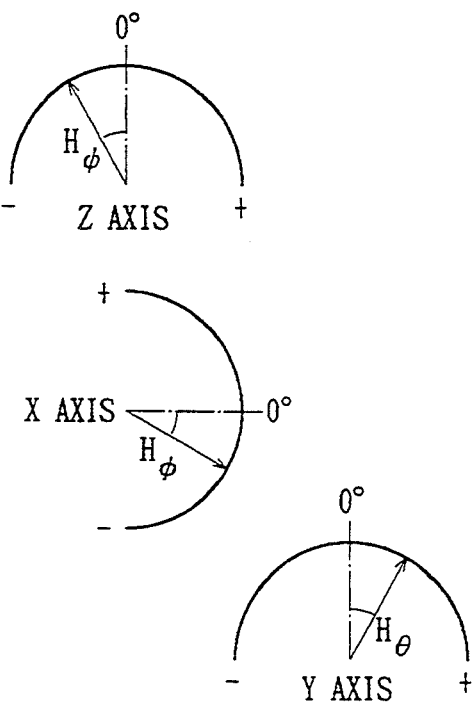

FIG. 20 is an illustration showing the principle of the head coordinate system with the subject being the center. Referring to FIG. 20, the head coordinate system detected by the head movement detecting portion 6 will be described. The head coordinate system includes two systems, that is, XY coordinate system realized by the translational movement of the subject with respect to the object of monitoring such as shown in FIG. 20(a), and a polar coordinate system based on the rotation movement of the head such as shown in FIG. 20(b). The amount of head movement in respective coordinate systems are defined as (Hx, Hy, Hz), (H$\psi$, H$\phi$, H$\theta$). In this embodiment, the direction toward the object of monitoring is represented by the Y axis, the horizontal movement is represented by the X axis and the vertical movement is represented by the Z axis, as an example. H$\phi$ represents the rotation of the X axis, that is, the movement of one's neck upward or downward. H$\theta$ represents the rotation of the Y axis, that is, the movement of inclining ones neck once from the left shoulder to the right shoulder. H$\psi$ represents rotation in the Z axis, that is, rotation of one's neck in the left or right direction.

The line-of-sight changes by the horizontal movement of the head (Hx, Hy, Hz), and when this movement is changed in the equivalent of rotation angle of the eye ball (Ex, Ey), the following equations are obtained.

$$Ex = 180/\pi \cdot \tan^{-1} Hx/(D+Hy) \quad (1)$$

$$Ey = 180/\pi \cdot \tan^{-1} Hz/(D+Hy) \quad (2)$$

where D: distance from the subject to the point of gazing.

When the neck is inclined by H$\theta$ to the left shoulder or to the right shoulder, the coordinate of the eye movement system rotates. Therefore, the eye movement coordinate system (Xe, Ye) inclined by H$\theta$ must be changed to the coordinate system (Xe', Ye') which is orthogonal to the original object of monitoring.

$$Xe' = Xe \cdot \cos H\theta + Ye \cdot \sin H\theta \quad (3)$$

$$Ye' = -Xe \cdot \sin H\theta + Ye \cdot \cos H\theta \quad (4)$$

The movement of the line-of-sight (Xh, Yh) realized by the head movement is represented by the following equations (5) and (6) derived from the equations (1) and (2).

$$Xh = Ex + H\psi \quad (5)$$

$$Yh = Ey + H\Phi \quad (6)$$

Therefore, the movement of the line-of-sight (Vx, Vy) taking the head movement into account is represented by the following equations (7) and (8), from equations (3) to (6).

$$Vx = Xe' + Xh \quad (7)$$

$$Vy = Ye' + Yh \quad (8)$$

By employing the equations (7) and (8) above, the ordinary movement of one's line-of-sight effected by combining head movement and eye movement can be reproduced.

Figure 21:
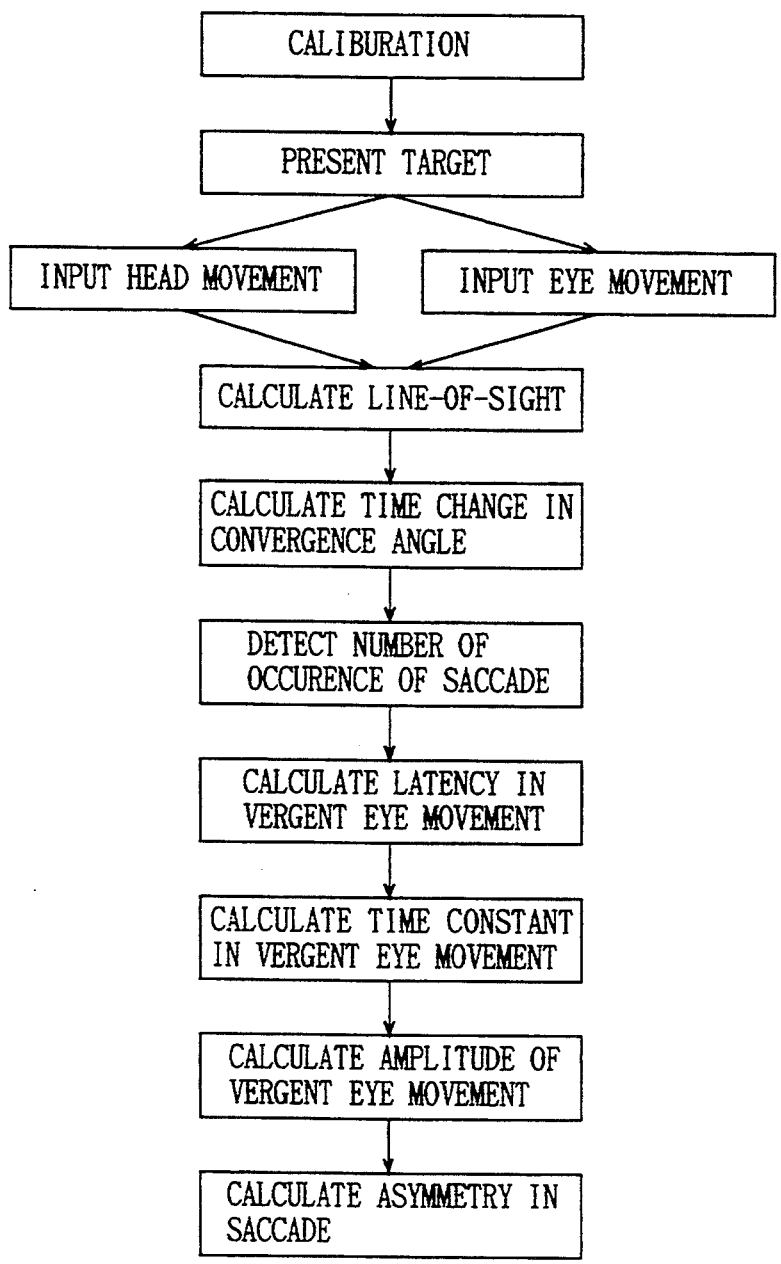
FIG. 21 is a flow chart showing operation of said another embodiment of the present invention.

FIG. 21 is a flow chart showing the operation of another embodiment of the present invention. In this embodiment, target in the depth direction are presented by the board 4 for calibration in the same manner as discussed above with reference to FIG. 1, the eye movement of the subject at that time is detected by the eye movement detecting portion 2, and the head movement of the subject is detected by the head movement detecting portion 6. The arithmetic operation portion 1 carries out the operations in accordance with the equations (1) to (8) on the basis of the detected head movement data and the eye movement data, and calculates parameters in the same manner as in the embodiment shown in FIG. 1. More specifically, in place of Xeye and Yeye in the embodiment shown in FIG. 1, the number of occurrence of saccade when the gaze is shifted in the depth direction, latency of the vergence eye movement, time constant of the vergence eye movement, amplitude of change of the convergence angle, monotony of change, asymmetry of saccade when symmetrical eye movement is required (for example, eye movement from target B to E) are calculated by using the gaze shift Vx and Vy calculated in accordance with the equations (7) and (8). The method of calculating these parameters are the same as those described with reference to FIG. 1, and diagnosis of Alzheimer's disease is done utilizing the measured values of these parameters generally.

As described above, according to the embodiment of the present invention, a target for depth perception is presented to a subject, movement of left and right eyes of the subject is detected and disorder in gaze shift in the depth direction of the subject is determined based on the detected output. Therefore, disorder in mechanism for controlling eye movement, depth perception, position in the brain of the subject can be easily detected, and accordingly, Alzheimer's disease can be discriminated from cerebrovascular disease.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An apparatus for examining gaze shift for detecting movement of line-of-sight in depth direction for a subject, comprising:

eye movement detecting means for detecting movement of left and right eyes of said subject;

target presenting means for presenting a target for depth perception to said subject;

target control means for controlling said target presenting means; and determining means responsive to a detection output from said eye movement detecting means when said subject is gazing at the target presented by said target presenting means, for determining whether there is a disorder in gaze shift in depth direction of said subject.

2. The apparatus for examining gaze shift in depth direction according to claim 1, further comprising:

head movement detecting means for detecting head movement of said subject; wherein said determining means includes means for determining whether there is a disorder in gaze shift in depth direction of said subject in response to a detection output from said eye movement detecting means and a detection output from said head movement detecting means.

3. An apparatus for examining gaze shift for detecting movement of line-of-sight in depth direction of a subject, comprising:

eye movement detecting means for detecting movement of left and right eyes of said subject;

target presenting means for presenting a target for depth perception to said subject;

target control means for controlling said target presenting means; and determining means responsive to a detection output from said eye movement detecting means when said subject is gazing at the target presented by said target presenting means, for determining whether there is a disorder in gaze shift in depth direction of said subject; wherein said determining means includes means for determining characteristics in gaze shift of said subject on the basis of time change of a convergence angle, in response to a detection output from said eye movement detecting means.

4. The apparatus for examining gaze shift in depth direction according to claim 3, wherein said determining means includes means for determining whether there is a disorder in gaze shift in depth direction by using at least one of latency in gaze shift, time constant, amplitude, change in the convergence angle, number of occurrence of saccade, and asymmetry of left and right eye movement, as characteristics of said eye movement.

5. An apparatus for examining gaze shift for detecting movement of line-of-sight in depth direction of a subject, comprising:

eye movement detecting means for detecting movement of left and right eyes of said subject;

target presenting means for presenting a target for depth perception to said subject;

target control means for controlling said target presenting means;

determining means responsive to a detection output from said eye movement detecting means when said subject is gazing at the target presented by said target presenting means, for determining whether there is a disorder in gaze shift in depth direction of said subject; and head movement detecting means for detecting head movement of said subject; wherein said determining means includes means for determining whether there is a disorder in gaze shift in depth direction of said subject in response to a detection output from said eye movement detecting means and a detection output from said head movement detecting means, and wherein said determining means includes means for determining characteristics of gaze shift of said subject on the basis of time change of the convergence angle in response to a detection output from said eye movement detecting means and a detection output from said head movement detecting means.

6. The apparatus for examining gaze shift in depth direction according to claim 5, wherein said determining means includes means for determining whether there is a disorder in gaze shift in depth direction by using at least one of latency of gaze shift, time constant, amplitude, change in convergence angle,number of occurrence of saccade, and asymmetry of left and right eye movement as said characteristics of the eye movement.

* * * * *